United States Patent [19]

Katz et al.

[11] Patent Number: 6,120,785
[45] Date of Patent: Sep. 19, 2000

[54] ANTIMYCOTIC ECTOPARASITICIDAL PRODUCT-EXTERNAL USE

[75] Inventors: Jaime Katz; Juana Fernandez Carbajales, both of Buenos Aires, Argentina

[73] Assignees: Omar Cristian Nunez; Ruben Fernando Iannantuono; Noa Vera Katz & Esteban Miguel Katz, all of, Argentina

[21] Appl. No.: 08/840,595

[22] Filed: Apr. 22, 1997

[30] Foreign Application Priority Data

Apr. 24, 1996 [AR] Argentina .................................. 336262

[51] Int. Cl.⁷ ...................................... A01N 25/02
[52] U.S. Cl. ......................... 424/405; 424/401; 424/406; 424/638; 514/499
[58] Field of Search .................... 424/405, 406, 424/401, 638; 514/499, 500

[56] References Cited

U.S. PATENT DOCUMENTS

| 3,873,703 | 3/1975 | Huber-Emden et al. | 424/258 |
| 4,009,254 | 2/1977 | Renold | 514/722 |
| 4,123,511 | 10/1978 | Heintze | 424/46 |
| 5,112,602 | 5/1992 | Miki et al. | 424/76.3 |
| 5,211,941 | 5/1993 | Komori et al. | 424/70 |

*Primary Examiner*—Neil S. Levy
*Attorney, Agent, or Firm*—D. Peter Hochberg

[57] ABSTRACT

Ectoparasiticidal and antimycotic product for external use, free from the risk of toxicity to humans or animals, and which offers favorable use conditions, consisting of the presentation of a copper oleate as an active agent, wherein the copper oleate is carried in an aqueous colloidal scattering manner. The formula of copper oleate preserves its insecticide and fungicide properties while having negligible cutaneous absorbtion.

3 Claims, No Drawings

ANTIMYCOTIC ECTOPARASITICIDAL PRODUCT-EXTERNAL USE

BACKGROUND OF THE INVENTION

1. Field of Invention

This invention refers to an ectoparasiticidal and antimycotic product for external use, which may be applied in human and veterinary medicine. More precisely, this invention consists of a copper oleate aqueous colloidal scatter.

2. Prior Art

The ectoparasiticidal products are drugs used in the treatment of skin infections caused by animal parasites. In humans, these pharmaceutical preparations are mainly insecticide and acaricide. The drugs currently available, used for the said purpose, are:

a) Lindane

The lindane or gamma benzene hexachloride has an insecticide and acaricide effect and is used for the treatment of the scabies. It is used at 1% in cream, lotion or shampoo. It is applied in fine layers on the neck and downwards and its effect may last from 4 to 8 or 12 hours depending on age and body area affected. A second application is made 5 days thereafter and another one ten days thereafter, following the birth cycle of the parasites. The lindane is used for the treatment of all pediculosis localizations. In general, only one application of lindane at 1% in shampoo, lotion or cream for 4 to 8 or 12 hours (according to the patient's age) is enough to eradicate the parasite, as it kills parasites and nits.

Unfortunately, the lindane has a quick transcutaneous absorption and high liposolubility, and it accumulates on the adipose tissue. It induces the mixed function oxidase system of the liver, it becomes debased slowly and lasts for a long time in the body. It acts on the presynaptic nervous terminals of the central nervous system, thus increasing the release of various neurotransmitters, and it may have consequences such as tremors, ataxia, convulsions and coma. It produces hepatoma in mice, although its carcinogenetic potential in human beings is doubtful.

b) Pirethrine

They are natural substances obtained from the pirethrum (chrysanthemus circerapiaefolium). The pirethoids are synthetic derivatives whose main examples are the permethrin and the decamethrin. Their efficacy is moderate since, although they are parasiticidal, they do not kill nits. They are presented as shampoo, lotion and cream. They are applied on the scalp for a time that varies from 10 minutes to 8 hours (depending on the patient's age) and then the nits affixed are taken out with a fine comb.

The permethrin acts on the membrane of the nervous cell of the parasite thus altering the sodium channel current which regulates the polarization of the membrane. This determines a late repolarization and the subsequent paralysis.

The decamethrin shares the same properties of the permethrin. The pirethrine and, in a higher proportion, the pirethoids, have marked allergenic properties (contact dermatitis and respiratory allergies).

c) Malathion

It is an irreversible organophosphorated anticholinesterasic insecticide. It is highly effective, but it is absorbed through the skin and it can cause a severe muscarinic intoxication if the directions for use are not strictly complied with, therefor its use is not advisable.

d) Benzyl benzoate

It is specially useful for the treatment of scabies and it is also used to treat pediculosis. It is irritating and frequently causes contact dermatitis, therefor its use is not advisable.

e) Diethiltoluamide

It is the most used insect repellent. Absorption through the skin is estimated between 10% and 15%. It produces allergic reactions and, in children, toxic encephalopathy, erythema and cutaneous ulcerations.

f) Copper

Copper is an oligoelement that takes part in many of the most important chemical reactions of the human body; among them, the ones related to erythropoyesis. The daily copper requirements are about 2.5 mg and they are easily covered with the diet. Any excess is easily eliminated by the body by means of a diminution of its gastrointestinal absorption by a complex homeostatic regulating mechanism.

The copper, used in the form of salts (oleate or sulfate) has antiseptic properties (sulfate), fungicide (sulfate and oleate) and parasiticidal (oleate). Copper salts have a not very powerful antiseptic activity, they rather have bacteriostatic effects when used in habitual concentrations.

The fungicide activity of the copper sulfate is specially used to destroy parasite mites of plants and, regarding the action mechanism, it is recognised that the copper cations precipitate the proteins and this is the reason for its local antiseptic effects, depending on the concentration used. The ectoparasiticidal activity is not clearly elucidated, but it is believed that the copper could act as a neurotoxic agent on the parasites. About 30% to 40% of the copper ingested is absorbed by the stomach and duodenum, followed by a quick transportation to the liver joined in a lax manner to the albumin. These complexes are dissociated in the hepatocytes membrane and the free copper is transferred inside the cells where it joins the apoceruloplasmine, and in this form it is excreted towards the serum.

The ceruloplasmine carries from 90 to 95% of the plasmatic copper and it is normally recycled in the liver, where it is degradated in the lysosomes thus releasing the copper, which is then excreted to the bile. The rest of the plasmatic copper is weakly joined to the albumin and is partly excreted to the bile. The quantity excreted by the kidney is very small as compared to the biliary excretion. The ingestion of excessive doses, for example 10 or more grams of copper sulfate causes symptoms derived from its local irritating activity at the gastrointestinal tract level; it produces nausea, vomiting, colic and diarrhea which may lead to collapse and shock. The ectoparaticidal formulae containing copper, known up to date, are mixtures of inflammable hydrocarbons, which contain a copper salt of a fatty acid dissolved in organic solvents. An apparent difficulty of these products is the high toxicity risk, since its formula favors cutaneous absorption and their permanence in the absorption place. On the other hand, due to is high irritating activity, contact of this product with the eyes, mucosas and open injuries must be avoided. Another adverse condition is the fact that it must be kept far from fire, due to its inflammability. Regarding its form of use, three or four spoonfuls of the mixture must be applied on the affected areas, leave overnight and remove with plenty of water and soap.

SUMMARY OF THE INVENTION

Due to the fact that the known products referred to pose the aforesaid problems, the purpose of this invention is to provide a product with an efficient external ectoparasiticidal and pediculicide activity, free from the risk of toxicity in the human being or in exposed animals and which may offer more favorable use conditions. This invention provides a solution to achieve the purported goal, thus constituting a creative conception, which is a novel formula of copper oleate that preserves its insecticide and fungicide properties, related in turn to practically null cutaneous absorption. The copper oleate is an active agent carried in an aqueous collidial scattering matter. Said formula, on which this patent is based, represents a creative response to the specific problems posed in relation to the environment and conditions in which these kinds of products are used, and essentially differs from the products currently known. Therefore, its industrial production will cover a current need of the market and represents a profitable novelty.

DETAILED DESCRIPTION OF THE PREFERRED EMBODIMENTS

This invention is illustrated by, but not limited to, the following examples:

EXAMPLE 1

Shampoo

Qualitative-quantitative formula expressed in hundredths:

| CHEMICAL DENOMINATION | PERCENTAGE (p/v) |
| --- | --- |
| 25% sodium laurylethersulfate | 30.00 g |
| Coconut fatty acid diethanolamide | 2.50 g |
| Copper oleate | 1.00 g |
| Fragrance | 0.25 g |
| Sufficient quantity of distilled water | 100.00 cc |

An additional advantage of this example is its form of use, as it consists of the following: apply, leave for a minute, wipe away and repeat the proceeding, if necessary.

EXAMPLE 2

Lotion

Qualitative-quantitative formula expressed in contents per 100 cc:

| CHEMICAL DENOMINATION | CONTENTS (p/v) |
| --- | --- |
| 25% sodium laurylethersulfate | 10.00 g |
| alkylolamide | 1.00 g |
| Copper oleate | 0.20 g |
| Polyvinylpyrrolidone | 0.50 g |
| Fragrance | 0.10 g |
| Glycerin | 1.00 g |
| Sufficient quantity of water | 100.00 cc |

EXAMPLE 3

Cream

Qualitative-quantitative formula expressed in contents per 100 g:

| CHEMICAL DENOMINATION | CONTENTS (p/v) |
| --- | --- |
| Stearic acid | 20.00 g |
| Glycerin | 40.00 g |
| Aqueous ammonia (26° Bé) | 3.00 g |
| Copper oleate | 1.00 g |
| Fragrance | 0.20 g |
| Sufficient quantity of water | 100.00 g |

Therefore, according to this invention, an external and pediculicide ectoparasiticidal product is provided, presenting the following advantages and benefits as compared to the existing products of that kind:

1) It has a high ectoparasiticidal and fungicide activity (specially on lice and mites), in addition to excellent cosmetic properties.
2) It is easy to apply, regardless of the final pharmaceutical formula.
3) Non-irratating to skin and mucous membrane.
4) A very low risk of allergenic episodes.
5) It may be used continuously.
6) It is virtually atoxic.
7) It may be used for any age.
8) The shampoo and the lotion have a pleasant clear emerald green color, thus favoring acceptance by consumers.

To sum up, this invention is based on a new concept consisting on the presentation of a known active agent (copper oleate) in aqueous colloidal scatter. In addition, this invention is not limited to the examples hereinabove described, as many changes and modifications can be introduced without departing from the essence of the scope of this invention. Consequently, in applying the external ectoparasiticidal and fungicide thus described and exemplified, modifications and/or improvements can be made, all of which must be deemed variants comprised within the scope of protection of this patent, which scope is essentially determined by the text of the following claims.

Having described and determined the nature and scope of this invention and the manner in which the same shall be applied in practice, we claim:

1. A composition of ectoparasiticidal and antimycotic activity which includes cooper oleate as an active agent wherein said copper oleate is vehiculized in the form of a watery colloidal dispersion, wherein said composition is a cream and wherein, per each 100 g. of composition the contents of the said active agent is within the 0.1 and 1.5 g. range; and the said watery colloidal dispersion is a compound of stearic acid, in a quantity within 15 and 25 g. range, glycerin, in a quantity within 30 and 50 g., aqueous ammonia (26° Bé) in a quantity within 2 and 4 cc, fragrance in quantity within 0 and 1 g., and distilled water in sufficient quantity to yield 100 g. of the composition.

2. A composition of ectoparasiticidal and antimycotic activity which includes copper oleate as an active agent wherein said copper oleate is vehiculized in the form of a watery colloidal dispersion, wherein said composition is a shampoo and wherein the proportion of the said active agent is within 0.1 and 2% of weight, and the watery colloidal dispersion is a compound of a 25% sodium laurylethersulfate aqueous solution in a proportion within 20 to 40% of weight of the composition, a coconut fatty acid diethanolamide in a proportion within 1 to 3% range in weight of the composition, fragrance in a proportion within 0 and 1% of weight of the composition, and sufficient quantity of distilled water until the 100% of the composition is completed.

3. A composition of ectoparasiticidal and antimycotic activity which includes copper oleate as an active agent wherein said copper oleate is vehiculized in the form of a watery colloidal dispersion, wherein said composition is a lotion and wherein, for every 100 cc of product, the contents of the said active agent is within the 0.1 to 0.3 g. range, and said watery colloidal dispersion is a compound of a 25% sodium laurylethersulfate aqueous solution in a quantity within 5 and 15 g., diethanolamide of coconut oil, in a quantity within 0.5 to 1.5 g., polyvinylpyrrolidone, in a quantity within 0.2 and 0.8 g., glycerin in a quantity within 0 and 1 g., and sufficient quantity of distilled water to yield 100 cc of the composition.

* * * * *